United States Patent
Aquila et al.

(10) Patent No.: US 6,242,653 B1
(45) Date of Patent: Jun. 5, 2001

(54) PROCESS FOR THE PREPARATION OF α-DIKETONES FROM KETOLS OR KETALS FROM KETOLS

(75) Inventors: Werner Aquila, Mannheim; Jörg Botzem, Limburgerhof; Melanie Brunner, Schifferstadt; Hartwig Fuchs, Ludwigshafen; Wolfgang Krause, Brühl; Klaus Pandl, Hambrücken; Ulrich Schäfer-Lüderssen, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/377,732

(22) Filed: Aug. 19, 1999

(30) Foreign Application Priority Data

Aug. 21, 1998 (DE) .............. 198 38 046

(51) Int. Cl.⁷ .................... C07C 45/29
(52) U.S. Cl. ............ 568/344; 568/320; 568/357; 568/361; 568/389; 568/399
(58) Field of Search .......... 568/320, 321, 568/322, 357, 360, 361, 399, 402, 403, 344, 414, 389

(56) References Cited

U.S. PATENT DOCUMENTS

| | | | |
|---|---|---|---|
| 2,043,950 | 6/1936 | De Simó et al. | 260/134 |
| 4,235,823 | 11/1980 | Dudeck et al. | 568/402 |
| 5,266,171 | 11/1993 | Hermeling | 204/59 R |

FOREIGN PATENT DOCUMENTS

| | | |
|---|---|---|
| 28 31 229 | 1/1980 | (DE) . |
| 28 31 595 | 1/1980 | (DE) . |
| 238 816 | 9/1986 | (DE) . |
| 296 274 | 11/1991 | (DE) . |
| 0 460 451 | 12/1991 | (EP) . |
| 0 430 406 | 5/1996 | (EP) . |
| 0 658 533 | 4/1998 | (EP) . |
| WO 96/04229 | 2/1996 | (WO) . |

OTHER PUBLICATIONS

Derwent Abstracts, SU 825 489, Apr. 30, 1981.
E. McCullagh, et al., Studies in Surface Science and Catalysis, vol. 82, pp. 853–860, "Diacetyl Synthesis by the Direct Partial Oxidation of Methyl Ethyl Ketone Over Vanadium Oxide Catalysts", 1994 (with Chemical Abstracts, AN 285011x).
R. Lindroos–Heinaenen, et al., Acta Chemica Scandinavica, vol. 45, pp. 543–545, "Kinetics of the Oxidation of Acetoin with Cerium(IV)", 1991 (with Chemical Abstract, AN 92 715).

Primary Examiner—Sreeni Padmanabhan
(74) Attorney, Agent, or Firm—Oblon, Spivak, McClelland, Maier & Neustadt, P.C.

(57) ABSTRACT

The process for the preparation of carbonyl compounds of the formula I

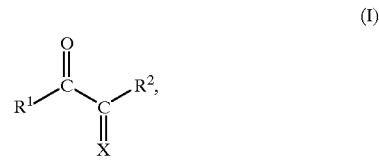

(I)

where $R^1$ and $R^2$ are a hydrocarbon radical, or $R^1$ and $R^2$ together are an unsubstituted or substituted alkylene group,
and X is=O or two alkoxy groups, comprises oxidizing alcohols of the formula II

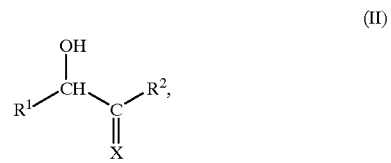

(II)

where $R^1$ to $R^2$ and X are as defined above,
with oxygen in the gaseous phase
a) at temperatures of from 270 to 600° C. on silver coated catalysts which comprise an abrasion-resistant coating of metallic silver on a core of inert support material, or
b) at temperatures of from 450 to 750° C. on silver crystals and/or copper crystals having a particle size of from 0.1 to 2.5 mm for a residence time of at most 0.1 second.

Also claimed is an advantageous overall process for the preparation of α-diketones, preferably diacetal, from the corresponding ketone, in particular methyl ethyl ketone, via the carbonyl compounds of the formula I where X is two alkoxy groups.

7 Claims, No Drawings

PROCESS FOR THE PREPARATION OF α-DIKETONES FROM KETOLS OR KETALS FROM KETOLS

The invention relates to an improved process for the preparation of ketones of the formula I

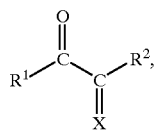

(I)

where $R^1$ and $R^2$ are a hydrocarbon radical, or
$R^1$ and $R^2$ together are an unsubstituted or substituted alkylene group
and X is=O or 2 alkoxy groups, by catalytic oxidation of the corresponding alcohols of the formula II

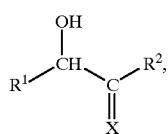

(II)

and, where necessary, subsequent hydrolysis of the resulting α-diketone monoketals, in particular to an industrially advantageous preparation of diacetyl.

The most important representatives of the ketones of the formula I are, because of their particular olfactory properties, 2,3-butanedione (diacetyl), 1,2-cyclopentanedione, 1,2-cyclohexanedione, 2,3-pentanedione, 2,3-hexanedione and 3,4-hexanedione and the monoketals of said 1,2-cycloalkanediones, but in particular diacetyl.

Due to the large demand for these compounds, in particular diacetyl, there has been no lack of attempts to find suitable preparation processes for these diketones. For example, U.S. Pat. No. 2,043,950 (1936) discloses a process for the catalytic oxidation of ketols in which ketols are reacted with molecular oxygen in the presence of solid oxidation catalysts at elevated temperature. Examples of solid oxidation catalysts are metals, metal alloys, metal salts and metal oxides, preferably elements from Group 3 of the Periodic Table of the Elements, such as Ti,
V, Cr, Mn, Fe, Co, Ni, Cu, Zn and Se, in particular Cu, CuO and Ag. According to the examples, 2,3-butanedione (diacetyl) is obtained from 3-hydroxy-2-butanone (acetoin) on CuO in yields of only 48%, based on reacted acetoin, and on activated copper in yields of from 43 to 82% of theory, depending on conversion. A disadvantage of this process is that, even when the preferred catalysts are used, good yields, e.g. of 82%, are obtained only for low conversions (25%), while in the case of good conversions (e.g. 77%) only low yields (e.g. 43%) are obtained.

The Derwent abstract of SU 825 489 (1979) discloses a process in which diacetyl is obtained in 75% yield by heating acetoin in aqueous solution with iron(III)chloride. Disadvantages of this process are the inadequate yields and the way in which the process is carried out, which is complex on an industrial scale.

Furthermore, DE-A 28 31 229 (1978) discloses a process for the preparation of diketones in which glycols are oxidized using oxygen in the presence of a catalyst consisting of two or more layers of silver and/or copper crystals of specific particle size and under specific conditions of temperature and catalyst compositions. A disadvantage of this process is firstly that the preparation of the 2,3-butanediol required as starting compound for diacetyl is very complex, making 2,3-butanediol very expensive, and secondly that in the reaction of 2,3-butanediol to diacetyl according to Example 3 of this patent, only yields of 76% of theory are obtained.

Furthermore, DE-A 28 31 595 (1978) discloses a process for the preparation of specific carbonyl compounds by oxidation of the corresponding alcohols with oxygen in the presence of silver crystals and/or copper crystals having a particle size of from 0.01 micrometer to 2.5 millimeter at from 450 to 700° C. and a residence time of at most 0.1 second. Essentially aliphatic or cycloaliphatic aldehydes or cycloalkanols are prepared by this process. However, the possibility of using this process to prepare α-ketocarboxylic esters is also described. In the only example in this respect, however, isobutyl α-oxo-isocaprate is only obtained in yields of 81% of theory.

DD 296 274 A (1990) discloses a process for the preparation of α-diketones in which α-acetoxy alkynes are oxidized in a carboxylic acid as solvent at from 0 to 100° C. in the presence of a Pd(II) salt, and the resulting α,β-unsaturated α-acetoxyketones are converted into α-diketones by subsequent hydrolysis.

Disadvantages of this process are the unsatisfactory yields and the industrially complex way in which the process is carried out.

Furthermore, C.A. 123:285011X (Abstract of Stud. Surf. Sci. Catal. 1994, 82, pages 853–60) discloses the preparation of diacetyl by partial oxidation of methyl ethyl ketone on a vanadium oxide catalyst. A disadvantage of this process is that relatively large amounts of acetic acid, acetaldehyde, methyl vinyl ketone, propionaldehyde and $CO_2$ are formed as byproducts.

In more recent experiments for the oxidation of acetoin with Ce(IV) in aqueous $HClO_4$, no diacetyl at all was isolated since it reacted further to give acetic acid (cf. Acta Chem. Scand. (1991), 45(5), pages 543–5).

Furthermore, Wo 96/04229-A1 discloses the oxidation of diols with gaseous fluorine to give 1,2-hydroxy-carbonyl compounds or to give 1,2-diones. A disadvantage of this process is that fluorine is a relatively expensive and dangerous-to-handle oxidizing agent.

EP 658 533 (1994) describes the oxidation of diols with o-iodoxybenzoic acid in dimethyl sulfoxide at from 40 to 50° C. A disadvantage of this process is that the oxidizing agent is difficult to prepare and is therefore very expensive.

Furthermore, EP 430 406 discloses the fermentative preparation of diacetyl and acetoin from sugars using lactic acid bacteria. A disadvantage of this process is that the yields which can be achieved are still inadequate.

It is an object of the invention to develop a highly advantageous process for the preparation of α-diketones from the corresponding ketols or ketals of these ketols, which permits the preparation of α-diketones, in particular diacetyl, even on an industrial scale in very good yields and space-time yields from relatively readily available starting compounds using low-cost oxidizing agents and on catalysts which are stable over a long period, with good sensory properties.

Relatively readily available starting compounds which have proven useful are ketols and ketals of ketols. For the preparation of diacetyl, which is in demand in particular as a butter aroma, these are acetoin, which is readily available by electrochemical oxidation of 2-butanone, and in particular 3,3-dialkoxy-2-butanols, which are very readily available, even on an industrial scale, by the process, described in EP 460 451, by electrochemical oxidation of methyl ethyl ketone (2-butanone) in the presence of alkanols, water and an auxiliary electrolyte.

The invention thus provides a process for the preparation of carbonyl compounds of the formula I

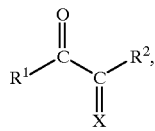
(I)

where $R^1$ and $R^2$ are a saturated or unsaturated, branched or unbranched aliphatic, cycloaliphatic, aromatic-aliphatic or cycloaliphatic-aliphatic radical having from 1 to 10 carbon atoms, preferably an alkyl group having from 1 to 4 carbon atoms, in-particular a methyl group or ethyl group, or $R^1$ and $R^2$ together are an alkylene group having from 3 to 10 carbon atoms which is unsubstituted or substituted by lower alkyl groups, preferably a propylene or butylene group, and X is=O or 2 alkoxy groups —$OR^3$, where $R^3$ is a saturated or unsaturated, branched or unbranched aliphatic radical having from 1 to 6 carbon atoms, preferably an alkyl group having from 1 to 4 carbon atoms, in particular a methyl group or ethyl group, or the two $R^3$ together are an alkylene group having from 3 to 6 carbon atoms which is unsubstituted or substituted by lower alkyl groups, in particular by methyl or ethyl groups, which comprises oxidizing alcohols of the formula II

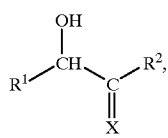
(II)

where $R^1$ to $R^3$ and X are as defined above, with oxygen in the gaseous phase
a) at temperatures of from 270 to 600° C., preferably from 300 to 550° C., on silver coated catalysts which comprise an abrasion-resistant coating of metallic silver on a core of inert support material, or
b) at temperatures of from 450 to 750° C., preferably from 480 to 600° C., on silver crystals and/or copper crystals, preferably on silver crystals, having a particle size of from 0.1 to 2.5 mm for a residence time of at most 0.1 second.

Suitable starting materials of the formula II for the novel process are thus compounds in which X is=O, i.e. ketols. In general, ketols are relatively readily accessible industrially by electrochemical oxidation of ketones. Examples include 3-hydroxy-2-butanone (acetoin), 2-hydroxy-1-cyclopentanone, 2-hydroxy-1-cyclohexanone, 2-hydroxy-3-pentanone 3-hydroxy-2-pentanone, 3-hydroxy-4-hexanone and 2-hydroxy-3-hexanone, in particular acetoin.

Advantageous starting materials of the formula II are also compounds in which X is 2 alkoxy groups. These can be obtained very advantageously, even industrially, by the electrochemical process described in EP 460 451 B1. Thus, for example, 3,3-dimethoxy-2-butanol, which is particularly suitable for the preparation of diacetyl, is obtained by this process from 2-butanone (methyl ethyl ketone) in a selectivity of 70% of theory (cf. Example 1A). From this, the novel process can be used to obtain 3,3-dimethoxy-2-butanone in yields above 90% (cf. Example 1B), which can be converted into diacetyl by alkaline or, preferably, acidic hydrolysis in a manner known per se in virtually quantitative yield. This is therefore a very advantageous overall process for the preparation of diacetyl from the readily available methyl ethyl ketone.

The invention thus also provides a process as defined above which comprises hydrolyzing the carbonyl compounds of the formula I, where X is two alkoxy groups, obtained in the oxidation of alcohols of the formula II where X is two alkoxy groups, and then hydrolyzing the products, in a manner known per se to give carbonyl compounds of the formula I where X is=O, and also such a process wherein the starting compounds are alcohols of the formula II where X is two alkoxy groups, which have been obtained by electrochemical oxidation of ketones of the formula III

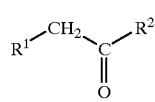
(III)

in the presence of $C_1$- to $C_4$-alkanols, water and auxiliary electrolytes.

The invention also provides a process for the preparation of carbonyl compounds of the formula I

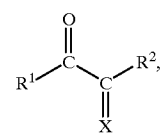
(I)

where $R^1$ and $R^2$ are a methyl group, or $R^1$ and $R^2$ together are an alkylene group having from 3 to 10 carbon atoms which is unsubstituted or substituted by lower alkyl groups, and X is=O, which comprises
A. using alcohols of the formula II

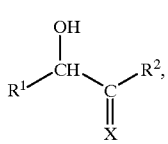
(II)

where $R^1$ to $R^2$ are as defined above, and

X is two alkoxy groups —$OR^3$, where $R^3$ is an alkyl group having from 1 to 4 carbon atoms, or the two $R^3$ together are an alkylene group having from 3 to 6 carbon atoms which is unsubstituted or substituted by lower alkyl groups, which alcohols have been prepared by electrochemical oxidation of ketones of the formula III

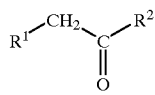

(III)

in the presence of $C_1$- to $C_4$-alkanols, water and auxiliary electrolytes,
B. oxidizing these with oxygen in the gaseous phase
   a) at temperatures of from 270 to 600° C., preferably from 300 to 550° C., in a tubular reactor or tube-bundle reactor on silver coated catalysts which comprise an abrasion-resistant coating of metallic silver on a core of inert support material, or
   b) at temperatures of from 450 to 750° C., preferably from 480 to 600° C., on silver crystals having a particle size of from 0.1 to 2.5 mm for a residence time of at most 0.1 second and
   c. hydrolyzing the resulting carbonyl compounds of the formula I where X is two alkoxy groups and hydrolyzing the products in a manner known per se to give carbonyl compounds of the formula I where X is=O.

Regarding Variant a) of the Novel Process

The silver coated catalysts which comprise an abrasion-resistant coating of metallic silver on a core of inert support material are catalysts which are prepared in a simple manner by coating inert support material, such as αaluminum oxide, silicon carbide or steatite, with silver by methods known per se, such as flame spraying, plasma spraying or vapor deposition. Particularly suitable coated catalysts consist, for example, of a support made of steatite, which is, for example, in the form of balls, rings or half-rings, with a deposited catalytic mass of silver, which constitutes, for example, from 0.1 to 10% by weight, based on the finished coated catalyst.

Preference is given to using silver coated catalysts which comprise elemental silver on inert material in the form of balls or comparable geometrical shapes, in particular those which comprise elemental silver on steatite beads. The diameter of the catalyst balls can be in the range from 1 to 10 mm, preferably from 1 to 5 mm.

Particularly advantageous reaction vessels for this process variant are individual reaction tubes or tube bundles which are filled with the solid catalyst particles. Preference is given to using reaction tubes which have an internal diameter of only from 0.5 to 30 mm, preferably from 10 to 20 mm. The mixture of the evaporated alcohol of the formula II and oxygen or, preferably, an oxygen-containing gas, in particular air, is passed through these tubes. They are surrounded by a medium which, at the start, provides the energy required to trigger the reaction and, during the reaction dissipates the heat formed in the exothermic reaction.

The length of the reaction tubes is generally at least 5 cm, preferably 10 to 60 cm.

The size of the catalyst particles must be adapted to the diameter of the reaction tubes used. The diameter of the catalyst particles is generally in the range from 1:10 to 1:5 relative to the internal diameter of the reaction tubes.

The gaseous reaction mixture leaving the reactor is worked up in a customary manner. For example, the hot reaction gases are absorbed immediately after leaving the reactor with a solvent or, preferably, in the condensed product mixture. The residence time of the gas mixture in the reaction tube is only from about 0.0005 to 1 second, preferably from 0.001 to 0.05 second.

Compared with the prior art, this variant of the novel process surprisingly provides, in a more simple and more economical manner, a better overall result in terms of yield, space-time yield and purity of the final materials. In particular, the amount of product relative to the catalyst used is very much greater, meaning that although the expensive noble-metal catalyst silver is used, the process is economical. The catalyst is easy to prepare and, because of its uniform spherical shape, permits simple filling of the reactor. A further advantage of the uniform shape of the catalyst is that, without further measures, an arranged, more dense packing in the reactor is achieved and in the case of tube-bundle reactors, each individual tube exhibits a similar pressure loss owing to the uniform packing. The identical pressure loss arising in the many tubes of a tube-bundle reactor leads to equal flow through the individual tubes and thereby evidently to a significant improvement in the selectivity of the reaction. Throughout the reaction, individual tubes do not experience higher space velocities, so that the service life of the catalyst is very long, several months in practice.

It was surprising that this method by itself can convert unstable hydroxy ketones, such as acetoin and ketal derivatives thereof, under the drastic conditions of oxidative dehydrogenation with high conversions and simultaneously selectivities greater than 90% of theory to the corresponding diketones or the monoketals of diketones respectively. An advantage when using hydroxy ketals of the formula II is the direct access to these starting compounds, which can otherwise only be obtained by means of a multistage reaction, from ketones.

Regarding Variant b) of the Novel Process

This process variant too uses free oxygen or gases containing free oxygen, in particular air, as oxidizing agent. Oxygen and alcohol II are expediently used in a molar ratio of from 0.25 to 0.9, preferably from 0.35 to 0.70 mol of oxygen per mole of alcohol of formula II.

The catalyst used is elemental silver and/or copper in the form of silver crystals and/or copper crystals having a diameter of approximately 0.1 to 2.5 mm. Use is generally made of mixtures of silver and/or copper crystals having various diameters.

Particular preference is given to using silver crystals having various diameters. The catalyst crystals can be used in an individual layer or in several superimposed layers. In the single-layer catalyst, the more coarsely particulate fraction of the catalyst crystals is homogeneously distributed in the layer.

When two, three or more catalyst layers are used, the individual layers differ with respect to the particle size of the catalyst crystals and in most cases also in the associated proportion by weight of the total catalyst. In a two-layer catalyst, there is expediently one layer of crystals having a particle size of from 0.1 to 0.75 mm and one with a particle size of from 0.75 to 2.5 mm.

If the catalyst is arranged in three layers, the particle sizes of the individual layers are, for example from 0.1 to 0.75 mm, from 0.75 to 1 mm and from 1 to 2.5 mm or from 0.2 to 0.4 mm, from 0.4 to 0.75 mm and from 0.75 to 1 mm.

For the preparation methods for silver, reference is made to Ullmann's Encyclopedia of Industrial Chemistry, Volume 15, pages 636 to 666. Silver can also be precipitated out from appropriate solutions, e.g. silver nitrate solutions, using precipitants, e.g. using hydrazine or formaldehyde, or be obtained by electrolysis.

The entire catalyst bed expediently lies on a gauze made of silver or stainless steel (preignited). In the case of large reactors having a diameter of more than 15 cm, the gauze is expediently corrugated prior to insertion.

The overall layer thickness of the catalyst is generally from about 5 to 50 mm, preferably from 10 to 30 mm.

In general, the process is carried out by passing a mixture of the vaporous alcohol of the formula II exiting the evaporation unit with oxygen or the oxygen-containing gas over the catalyst at the reaction temperatures. The temperature at the catalyst is expediently measured using thermocouples.

The pressure prevailing during the reaction is unimportant. The reaction is therefore usually carried out at atmospheric pressure. It can, however, also be advantageous to work at reduced pressure if it is difficult to evaporate the alcohol of the formula II which is to be oxidized.

For some reactions, it has proven advantageous to deposit on the catalyst further small amounts of phosphorus salts, such as phosphates or polyphosphates, by sprinkling or by deposition from solutions.

Alkali metal or alkaline earth metal phosphates or pyrophosphates, such as $Na_4P_2O_7$, $Li_3PO_4$, $Mg_3(PO_4)_2$ or $Ca_3(PO_4)$ are used for this purpose. The amount of phosphorus compound used is from 0.05 to 100 mg of phosphorus per gram of catalyst.

The novel process enables the preparation of the diketones which are in demand because of their particular olfactory properties, such as diacetyl, 1,2-cyclopentanedione, 1,2-cyclohexanedione, 2,3-pentanedione, 3,4-hexanedione and 2,3-hexanedione and also the monoketals of 1,2-cycloalkanediones in a simple manner in high selectivity at very high conversions and space-time yields and with good sensory properties.

EXAMPLE 1

A) Preparation of 3,3-dimethoxy-2-butanol

An undivided electrolysis cell (stacked plate cell) with 10 gaps, 1.45 dm² area per electrode, a carbon felt KFD-2-anode and a graphite plate MKUS P-10-cathode (both from SGL Carbon, 0.9 mm polypropylene mesh spacer) was used to electrochemically oxidize an electrolyte solution consisting of 1000 g of 2-butanone, 45 g of KI, 10 g of KOH, 5 g of water and 1950 g of methanol at temperatures of <20° C., a current strength of 3.06 A/dm², an amount of electricity of 1.5 F and a throughput of from 45 to 60 I/(h * gap).

The 3,3-dimethoxy-2-butanol was obtained here in a selectivity of 70% of theory at a conversion of 58%.

B) Preparation of 3,3-dimethoxy-2-butanone 553 g of 3,3-dimethoxy-2-butanol were evaporated per hour (h) and reacted with air (0.6 mol of oxygen per mole of starting material) at 500° C. on a three-layer bed consisting of 8 g of silver particles having a diameter of from 0.75 to 1 mm, 14 g having a diameter of from 0.4 mm to 0.75 mm and 6 g having a diameter of from 0.2 to 0.4 mm (bulk volume 6 ml). The space velocity of the catalyst was 20 kg of starting material/kg.h. 595 g of a mixture were obtained, which consisted of 82.5% of 3,3-dimethoxy-2-butanone and 1.2% of diacetyl. This corresponds to a yield of desired product of 91.34% of theory, and 90.04% of theory of 3,3-dimethoxy-2-butanone and 1.31% of theory of diacetyl.

C) Preparation of Diacetyl from 3,3-dimethoxy-2-butanone

With the addition of water and/or dilute mineral acids, the 3,3-dimethoxy-2-butanone is cleaved during the subsequent distillative workup. If the distillation column is suitably arranged, the diacetyl is produced in a purity of >99%.

EXAMPLE 2

Oxidation of 3-hydroxy-2-butanone to Give Diacetyl 14.5 g of a coated catalyst, which comprised 6% by weight of silver as a continuous coating of metallic silver on steatite balls having a diameter of from 0.2 to 0.25 mm, were introduced into a tubular reactor having a diameter of 11 mm to form a 10 cm-high catalyst layer. Acetoin (comprising about 12% of water) and oxygen in the form of air in the molar ratio given in the table were passed through this catalyst layer in a space velocity given in the table at the reaction temperatures given in the table.

The conversions of acetoin achieved hereby and the achieved yields of diacetyl per converted acetoin (selectivities) are given in the table below.

TABLE

| Example | Temperature [° C.] I = initial temperature F = final temperature | Acetoin: $\frac{1}{2}O_2$ molar ratio | Weight hourly space velocity t/m²·h | Conversion [%] | Selectivity [%] |
|---|---|---|---|---|---|
| 2a | I 370 F540 | 1:1.10 | 0.52 | 90.2 | 90.0 |
| 2b | I 360 F533 | 1:1.12 | 0.51 | 91.7 | 92.1 |
| 2c | I 361 F 534 | 1:1.09 | 0.52 | 87.8 | 89.3 |
| 2d | I 324 F 537 | 1:1.11 | 0.51 | 83.6 | 91.4 |
| 2e | I 329 F 518 | 1:1.12 | 0.51 | 76.9 | 95.7 |
| 2f | I 305 F 543 | 1:1.12 | 0.51 | 79.8 | 91.4 |
| 2g | I 289 F 572 | 1:1.10 | 0.52 | 85.1 | 89.3 |
| 2h | I 408 F 499 | 1:1.13 | 0.51 | 66.1 | 93.9 |
| 2i | I 427 F 487 | 1:1.13 | 0.50 | 65.3 | 96.1 |
| 2k | I 424 F 458 | 1:1.10 | 0.52 | 47.9 | 97.6 |

EXAMPLE 3

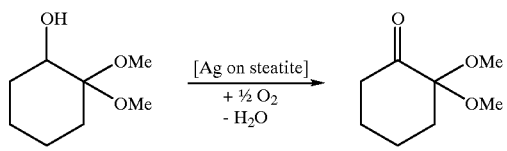

55 g (0.34 mol) of 2,2-dimethoxycyclohexanol were evaporated per h and passed with air (0.65 mol of oxygen per mole of starting material) at 500° C. over a short-tube reactor (length 10 cm; diameter: 11 mm) packed with 17 g of silver on steatite beads (6% Ag). The weight hourly space velocity was 3.2 kg of starting material/(kg·h). 54 g of a mixture of 88% of 2,2-dimethoxycyclohexanone and 6% of cyclohexane-1,2-dione were obtained per hour. The conversion of starting material was complete.

This corresponds to a yield of 94.5% of theory of desired product, and to a yield of 88.5% of 2,2-dimethoxycyclohexanone and 6% of cyclohexane-1,2-dione.

We claim:
1. A process for the preparation of carbonyl compounds of the formula I

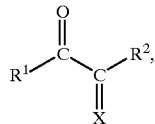
(I)

where $R^1$ and $R^2$ are a branched or unbranched aliphatic, cycloaliphatic, aromatic-aliphatic and cycloaliphatic-aliphatic radical having from 1 to 10 carbon atoms, or
$R^1$ and $R^2$ together are an alkylene group having from 3 to 10 carbon atoms which is unsubstituted or substituted by lower alkyl groups,
and X is=O or 2 alkoxy groups —$OR^3$, where $R^3$ is a saturated or unsaturated, branched or unbranched aliphatic radical having from 1 to 4 carbon atoms, or the two $R^3$ together are an alkylene group having from 3 to 6 carbon atoms which is unsubstituted or substituted by lower alkyl groups,
which comprises oxidizing alcohols of the formula II

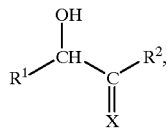
(II)

where $R^1$ to $R^3$ and X are as defined above,
with oxygen in the gaseous phase
a) at temperatures of from 270 to 600° C. on silver coated catalysts which comprise an abrasion-resistant coating of metallic silver on a core of inert support material, or
b) at temperatures of from 450 to 750° C. on silver crystals and/or copper crystals having a particle size of from 0.1 to 2.5 mm for a residence time of at most 0.1 second.

2. A process as claimed in claim 1, which comprises oxidizing alcohols of the formula II, where X is=O, and $R^1$ and $R^2$ are as defined above, on silver coated catalysts which comprise elemental silver on spherical inert material.

3. A process as claimed in claim 2, which comprises oxidizing alcohols of the formula II, where X is=O, and R1 and $R^2$ are as defined above, in a reaction tube or tube bundle on silver coated catalysts which comprise elemental silver on steatite beads.

4. A process as claimed in claim 1, which comprises oxidizing alcohols of the formula II, where X is two alkoxy groups each having from 1 to 4 carbon atoms, with oxygen on silver crystals having a particle size of from 0.1 to 2.5 mm.

5. A process as claimed in claim 1, which further comprises hydrolyzing the carbonyl compounds of the formula I, where X is two alkoxy groups, obtained in the oxidation of alcohols of the formula II where X is two alkoxy groups, to give carbonyl compounds of the formula I where X is=O.

6. A process as claimed in claim 1, wherein the starting compounds are alcohols of the formula II where X is two alkoxy groups, which have been obtained by electrochemical oxidation of ketones of the formula III

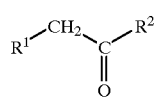
(III)

in the presence of $C_1$- to $C_4$-alkanols, water and auxiliary electrolytes.

7. A process for the preparation of carbonyl compounds of the formula I:

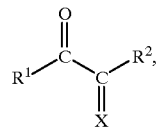
(I)

where $R^1$ and $R^2$ are a methyl group, or $R^1$ and $R^2$ together are a $C_{3-10}$-alkylene group or a $C_{3-10}$-alkylene group substituted by lower alkyl groups, and X=O, which comprises:
A. electrochemically oxidizing a ketone of formula III:

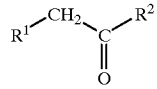
(III)

in the presence of $C_1$- to $C_4$-alkanols, water and auxiliary electrolytes, thereby preparing an alcohol of formula II:

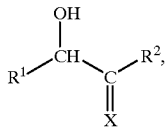
(II)

wherein $R^1$ and $R^2$ are as defined above and X is two alkoxy groups —$OR^3$, and wherein $R^3$ is an alkyl group having from 1 to 4 carbon atoms, or the two $R^3$ groups together are a $C_{3-6}$-alkylene group or a $C_{3-6}$-alkylene group substituted by lower alkyl groups;
B. oxidizing an alcohol of formula II with oxygen in the gaseous phase under the conditions of:
a) at a temperature of 270 to 600° C. on a silver coated catalyst which comprises an abrasion-resistant coating of metallic silver on a core of inert support material, or
b) at a temperature of 450 to 750° C. on silver crystals having a particle size of from 0.1 to 2.5 mm for a residence time of at most 0.1 second; and
C. hydrolyzing the resulting carbonyl compound of formula I where X is two alkoxy groups to a carbonyl compound of formula I where X=O.

* * * * *